United States Patent [19]

Thalhammer et al.

[11] Patent Number: 5,648,490

[45] Date of Patent: Jul. 15, 1997

[54] PROCESS FOR THE PREPARATION OF 5-FORMYLAMINOPYRIMIDINES

[75] Inventors: Franz Thalhammer; Jürgen Graefe, both of Trostberg, Germany

[73] Assignee: SKW Trostberg Aktiengesellschaft, Trostberg, Germany

[21] Appl. No.: 413,132

[22] Filed: Mar. 28, 1995

[30] Foreign Application Priority Data

Mar. 28, 1995 [DE] Germany .................. 44 10 678.5

[51] Int. Cl.$^6$ .................................................. C07D 239/50
[52] U.S. Cl. ............................ 544/320; 544/298; 544/322; 544/323; 544/333
[58] Field of Search .............................. 544/298, 322, 544/333, 320, 323

[56] References Cited

U.S. PATENT DOCUMENTS 4,948,890  8/1990  Schneider ...................... 544/320

FOREIGN PATENT DOCUMENTS 267594   5/1988  European Pat. Off. .
0304004  8/1988  European Pat. Off. .

OTHER PUBLICATIONS

Laurent Fraisse et al., Long–Chain–Substituted Uric Acid and 5,6–Diaminouracil Derivatives as Novel Agents Against Free Radical Processes: Synthesis and in Vitro Activity, Sep. 22 1992, pp. 1465–1473.
J. Medicinal Chemistry, 1993, vol. 36.
A. Yamazaki, Synthesis of 9–(4'Hydroxybutyl)–2–amino–6–hydroxy–purine 4'–Phosphate') Apr. 1969, pp. 1268–1270, Chem. Pharm. Bull. 17(6), 1969.

Shinozuka et al., Nucleoside Complexing . . . Synthetic Betains, 1985, pp. 141–150. Inorganic Chimica Acta, vol. 100, 1985.
J.C. Sircar et al., 8–amino–9–substituted guanines: Potent purine nucleoside phosphorylase (PNP) inhibitors, 1987, pp. 253–256. Agent and Action vol. 21.
Corbett et al. J. Org. Chem. 46(2), pp. 466–468 1981.

Primary Examiner—Yogendra N. Gupta
Attorney, Agent, or Firm—Felfe & Lynch

[57] ABSTRACT

Disclosed is a process for the preparation of 5-formylaminopyrimidines of the general formula:

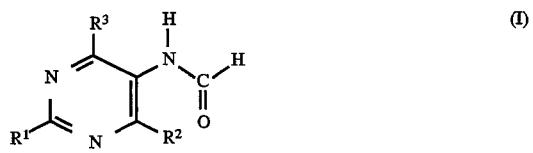

in which $R^1$, $R^2$ and $R^3$ are the same or different and signify H, OH, SH, $NH_2$, alkylamino, halogen, O-alkyl, S-alkyl or alkyl, as well as aryl, and alkyl is an aliphatic radical containing up to 4 carbon atoms, from the corresponding 5-nitrosopyrimidines of the general formula:

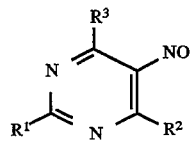

in which $R^1$, $R^2$ and $R^3$ have the same meanings as above, wherein the starting compound is subjected to a reductive formylation in the presence of a noble metal catalyst, as well as of formic acid and of a salt thereof.

21 Claims, No Drawings

PROCESS FOR THE PREPARATION OF 5-FORMYLAMINOPYRIMIDINES

BACKGROUND OF THE INVENTION

The present invention is concerned with a process for the preparation of 5-formylaminopyrimidines from the corresponding 5-nitrosopyrimidines by reductive formylation.

The hydrogenation of substituted 5-nitrosopyrimidines according to various methods is known. As large scale process, noble metal-catalysed hydrogenation with hydrogen under pressure is usually employed. Thus, for example, to DE-PS 36 38 635, there is described the catalytic hydrogenation of 2,4-diamino-6-hydroxy-5-nitrosopyrimidine (DAHNP) and the reaction of the 2,4,5-triamino-6-hydroxypyrimidine (TAHP) thereby obtained with formic acid to give 2,4-diamino-5-formylamino-6-hydroxypyrimidine (DAFHP). The reaction is carried out in aqueous solution at a temperature of from 20° to 80° C. and at a hydrogen pressure of from 1.4 to 21 bar in the presence of known hydrogenation catalysts. Over the course of the reaction period, 0.8 to 1.5 mol of base must be added continuously per mol of DAHNP. In the case of this reduction method, it is disadvantageous that, on the one hand, a high hydrogen pressure is used, which makes necessary the use of expensive autoclaves or of loop reactors, and, on the other hand, the addition of equimolar amounts of bases for dissolving the starting compound gives rise to an additional amount of salt resulting in a burdening of the environment.

DE-OS 37 27 508 describes the reduction of 5-nitrosopyrimidine derivatives with sodium dithionite and subsequent formylation to give the corresponding 5-formylaminopyrimidines. This method has the disadvantage that, besides the liberation of sulphur dioxide, large amounts of sulphur-containing salts are also obtained as by-products so that the economic efficiency necessary for a technical production is not obtained.

Therefore, it is an object of the present invention to provide a process for the preparation of 5-formylaminopyrimidines from the corresponding 5-nitrosopyrimidines which does not suffer from the above-mentioned disadvantages of the prior art but rather permits, in an economically meaningful and environmentally acceptable way, under pressureless conditions, the conversion of substituted 5-nitrosopyrimidines into 5-formylaminopyrimidines.

THE INVENTION

According to the present invention, the above stated object is achieved by subjecting the starting compounds to a reductive formylation in the presence of a noble metal catalyst, as well as of formic acid and of a formate. Surprisingly, we have found that, in this way, 5-formylaminopyrimidines can be prepared in high yields and with good purity in a one-step process from the corresponding nitroso derivatives without the use of pressure and of gaseous hydrogen being necessary.

In the case of the process according to the present invention, a starting compound there is used a 5-nitrosopyrimidine of the general formula:

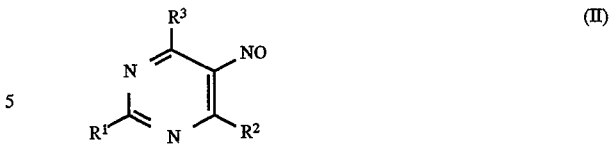

in which $R^1$, $R^2$ and $R^3$ can be the same or different and signify H, OH, SH, $NH_2$, alkylamino, halogen, O-alkyl, S-alkyl or alkyl, as well as aryl, and alkyl is an aliphatic radical containing up to 4 carbon atoms. As aryl radicals, phenyl radicals are preferred which can therefor optionally be substituted.

The starting compound is suspended in water and/or an organic solvent, the organic solvent preferably being formamide and/or formic acid. The formic acid can also be used as a dilute aqueous solution with a concentration of 20 to 100% by weight. The concentration of the starting compound in the suspension can be varied within wide limits and is preferably 0.1 to 3.0 mol and especially 1.0 to 2.0 mol of nitroso compound per liter of solvent.

If working is not carried out in formic acid as solvent, formic acid is added to this suspension, preferably in an amount of from 1.0 to 10.0 mol and especially preferably of from 3.5 to 5.0 mol per mol of nitroso compound. The addition can be made before or during the reaction.

As formic acid salts, used formates of alkali metals, alkaline earth metals, ammonia or amines are preferably used. Sodium or potassium formate, ammonium formate or trialkylammonium compounds, for example triethylammonium formate, are especially preferred. The use of ammonium formate is especially recommended when the mother liquor is to combusted since, in this case, a residue-free combustion is possible. The formate is are preferably used in a mol ratio of 0.1 to 5, referred to the nitroso compound. The formate can be added in solid or dissolved form.

Furthermore, the formate can also be formed in situ by the addition of, for example, an aqueous solution of sodium hydroxide or of an appropriate amine to the formic acid-containing suspension. In this case, the formic acid necessary therefor must be present in addition to the above-mentioned amount.

To the suspension is added a noble metal catalyst, for example one based upon palladium or platinum, on a carrier material. The amount of catalyst added depends upon the particular content of noble metal. Commercially available catalysts have proven to be suitable. The catalyst is preferably used in such an amount that the amount of pure noble metal amounts to 200 to 2000 mg per kg of nitroso compound used. Active carbon has proved to be useful as carrier material for the noble metal catalyst, the noble metal content thereby being from 0.1 to 10% by weight. Especially preferred is the use of a catalyst with a palladium content of about 5% by weight on active carbon, especially with a water content of 40 to 60% by weight, which is used in an amount of from 1 to 3% dry weight, referred to the nitroso compound.

After the addition of the catalyst carbon dioxide is liberated, while stirring even at ambient temperature. Subsequently, the reaction temperature is adjusted and is preferably from 50° to 200° C. and especially from 90° to 110° C. Dependent upon the reaction conditions and upon the reaction components, the reaction is ended after 1 to 10 hours and usually after 2 to 3 hours, the complete reaction being recognisable by the decolorisation of suspension which, in most cases, is intensively red to violet colored.

For many subsequent reactions, the separating off of the catalyst after conclusion of the reductive formylation is not absolutely necessary if, in the subsequent process steps, there is a possibility to do so. As a rule, the 5-formylaminopyrimidines obtained have such a high degree of purity that, without further purification, they can be used for the synthesis of subsequent products, for example of purines.

If a separation of the catalyst is desired for the isolation of the reaction product, it is recommended to cool the suspension, to separate off the solid material, for example by filtration, and then to wash the filter cake with water. For the separation of the noble metal catalyst, the filter cake is then dissolved in a dilute, preferably 5% by weight aqueous sodium hydroxide solution, the catalyst is filtered off and the product is again precipitated out by the addition of an acid, preferably formic acid.

In many cases, it is also possible to keep the product in solution by appropriate dilution. In this case, the catalyst is preferably separated off from the hot solution and the product allowed to crystallize out by concentration of the solution and/or by cooling. In this way, a very pure product is obtained.

According to the present invention, it is possible to prepare 5-formylaminopyrimidines in a yield of up to 98% and with a degree of purity of more than 98%. On the basis of these high yields and of the relatively low technical expense (no pressure reaction and no use of hydrogen), the process according to the present invention is especially well suited for carrying out on a technical scale.

The following Examples are given for the purpose of illustrating the present invention:

EXAMPLE 1

31.7 g (0.2 mol) 2,4-diamino-6-hydroxy-5-nitrosopyrimidine (DAHNP) of were suspended in 100 ml of water and 37.2 g (0.8 mol) of 98% formic acid added thereto. Subsequently, 6.4 g (0.1 mol) of ammonium formate were stirred in and 1.0 g of a palladium catalyst on active carbon (type E10 R/W, 5% palladium, 50% moisture) added thereto. A slight gas evolution already commenced at ambient temperature. The temperature was increased up to reflux at 100° C. and maintained for 2 hours with good stirring. After about 1.2 hours, the initially pink-colored suspension became grey colored because of the content of catalyst. Subsequently, the reaction mixture was cooled to 10° C. and the crystalline slurry filtered off with suction through a Buchner funnel. The filter cake was dissolved in 160 ml of a 5% by weight aqueous solution of sodium hydroxide and the noble metal catalyst separated off by filtration. By means of the addition of 9.3 g of 85% by weight formic acid, the product was again precipitated out, subsequently filtered off, washed twice with, in each case, 15 ml of water and dried in a vacuum at 60° C.

In this way, there were obtained 32.1 g of colorless crystals with a content of 98.1% 2,4-diamino-5-formylamino-6-hydroxypyrimidine. This corresponds to a yield of 94.8% of theory.

EXAMPLE 2

31.7 g (0.2 mol) of DAHNP were suspended in 100 ml of 85% formic acid. 44.3 g (0.6 mol) of ammonia in the form of a 23% aqueous solution were added dropwise thereto and 1.0 g of the palladium catalyst according to Example 1 added thereto. With carbon dioxide evolution and vigorous stirring, the reaction mixture was heated to 100° C. and this temperature maintained for 3 hours.

After 2 hours, the suspension had decolorised. After cooling, the conversion into DAFHP was determined in a sample by means of HPLC, a content of 32.3 g being determined. This corresponds to a conversion of 96%, it not being possible to detect residues of the starting compound or of by-products.

EXAMPLE 3

31.7 g (0.2 mol) of DAHNP were suspended in 100 ml formamide and 38.4 g (0.8 mol) of ammonium formate were added thereto. After the addition of 37.2 g (0.8 mol) of formic acid, 1.0 g of the palladium catalyst according to Example 1 was stirred in and the reaction mixture heated to 100° C. With gas evolution, the suspension decolorised within the course of 3 hours. After cooling, the conversion was determined in a sample by means of HPLC. This gave a conversion to DAFHP of 96.2%. Neither the starting compound nor by-products could be detected.

EXAMPLE 4

37.2 g (0.8 mol) of formic acid and 20.5 g (0.3 mol) of sodium formate were added to a suspension of 31.7 g (0.2 mol) of DAHNP in 100 ml of water. After the addition of 1.0 g of the palladium catalyst according to Example 1, the reaction mixture was heated under reflux. With good stirring, carbon dioxide was thereby liberated. After 2 hours, the suspension had decolorised and, after another hour, it was cooled. 33.6 g of gray crystals were obtained by filtration. These were dissolved in 160 ml of a 5% solution of sodium hydroxide, the catalyst was filtered off and the product again precipitated out by the addition of 9.5 g of 98% formic acid. After cooling to 0° C., there were obtained 33.0 g (97.8% of theory) of DAFHP as a colorless, finely crystalline powder.

EXAMPLE 5

31.7 g (0.2 mol) of DAHNP were suspended in 1500 ml of water and then 37.2 g (0.8 mol) of formic acid, 38.7 g (0.6 mol) of ammonium formate and 1.0 g of the palladium catalyst according to Example 1 added thereto. The suspension was heated to reflux with vigorous stirring. After 3 hours, a black solution was obtained. For the separation of the catalyst, this solution was filtered hot and slowly cooled, colorless crystals of DAFHP thereby precipitating out. Crystallization was completed by cooling to 0° C. and the crystals filtered off with suction. There were obtained 26.7 g (79% of theory) of colorless crystals with a degree of purity of 99.1%.

EXAMPLE 6

A suspension of 7.9 g (0.05 mol) of 2,4,6-triamino-5-nitrosopyrimidine in 50 ml of water was mixed with 3.25 g (0.05 mol) of ammonium formate, 13.9 g (0.3 mol) of formic acid and 0.5 g of the palladium catalyst according to Example 1. This mixture was heated for 4 hours to 100° C. After cooling, the catalyst was filtered off, the filtrate concentrated to about 25 ml and neutralised with about 10 ml of 25% aqueous sodium hydroxide solution to pH 7.5. A crystal slurry thereby resulted which was filtered off with suction. In this way, there were obtained 8.1 g (87% of theory) of pale beige crystals of 2,4,6-triamino-5-formylaminopyrimidine hydrate.

Analysis: calc.: C, 32.25%; H, 5.41%; N, 45.14%; found: 32.19%; 5.60%; 44.98%.

EXAMPLE 7

15.5 g (0.1 mol) of 4,6-dihydroxy-2-methyl-5-nitrosopyrimidine were suspended in 50 ml of water, 18.2 g (0.4 mol) of formic acid and 3.4 g (0.05 mol) of sodium formate added thereto and, while stirring, 0.5 g of the palladium catalyst according to Example 1 added thereto. Until decolorisation had taken place, the colored suspension was then heated to 100° C., cooled to 10° C. and the crystals obtained filtered off with suction. The filter cake, which still contained catalyst, was recrystallized from water with hot filtration. The crystals were dried in a vacuum at 60° C. and obtained in a yield of 13.5 g (80% of theory).

Analysis: calc.: C, 42.60%; H, 4.17%; N, 24.84%; found: 42.58%; 4.29%; 24.69%.

It will be understood that the specification and examples are illustrative but not limitative of the present invention and that other embodiments within the spirit and scope of the invention will suggest themselves to those skilled in the art.

We claim:

1. A process for the preparation of a 5-formylaminopyrimidine of the formula:

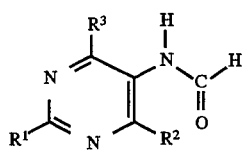

in which $R^1$, $R^2$ and $R^3$ are the same or different and signify H, OH, SH, $NH_2$, alkylamino, halogen, O-alkyl, S-alkyl, alkyl, aryl, and alkyl is an aliphatic radical containing up to carbon atoms, comprising consisting essentially of:

subjecting a corresponding 5-nitrosopyrimidine of the formula

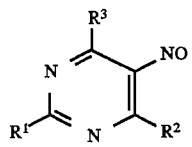

in which $R^1$, $R^2$ and $R^3$ have the same meaning as above, to a reductive formylation in the presence of a noble metal catalyst, formic acid and of a salt thereof.

2. The process of claim 1, wherein the reductive formylation is carried out in water and/or an organic solvent.

3. The process of claim 2, wherein the organic solvent is formamide and/or formic acid.

4. The process of claim 1 wherein the formic acid is used in an amount of 1.0 to 10.0 moles per mole of the nitrosopyrimidine.

5. The process of claim 4, wherein 3.5 to 5 moles of formic acid is used per mole of the nitrosopyrimidine.

6. The process of claim 1 wherein the formic acid salt is a formate of an alkali metal, alkaline earth metal, ammonia or an amine.

7. The process of claim 1 wherein the formate is used in an amount of from 0.1 to 5 moles per mole of the nitrosopyrimidine.

8. The process of claim 1 wherein the catalyst is based on palladium or platinum.

9. The process of claim 8 wherein the catalyst contains pure noble metal in an amount of 200 to 2000 mg per kg of the nitrosopyrimidine.

10. The process of claim 1 wherein the catalyst is used on an active carbon carrier material and the catalyst has a content of noble metal of 0.1 to 10% by weight.

11. The process of claim 1 wherein the reaction temperature is adjusted to 50° to 200° C.

12. The process of claim 11 wherein the reaction temperature is adjusted to 90° to 110° C.

13. The process of claim 1 further comprising filtering off the catalyst from the reaction mixture and crystallizing out the product from the solution by concentration and/or cooling.

14. The process of claim 1 wherein an aqueous sodium hydroxide solution is added to the reaction mixture until the product has completely dissolved, the catalyst is then filtered off from the dissolved product and subsequently the formylamino compound is precipitated out with an acid.

15. The process of claim 14 wherein the acid used for precipitating out the formylamino compound is formic acid.

16. The process of claim 1 wherein the concentration of the 5-nitrosopyrimidine is 0.1 to 3.0 moles per liter of solvent.

17. The process of claim 16 wherein the concentration of the 5-nitrosopyrimidine is 1.0 to 2.0 moles per liter of solvent.

18. The process of claim 1 wherein the 5-nitrosopyrimidine is selected from the group consisting of 2,4-diamino-6-hydroxy-5-nitrosopyrimidine or 2,4,6-triamino-5-nitrosopyrimidine.

19. The process of claim 1 wherein the noble metal catalyst, the formic acid and salt are simultaneously present during the reductive formylation.

20. The process of claim 1 wherein the reductive formylation of 5-nitrosopyrimidine to the 5-formyl aminopyrimidine is a one-step process.

21. The process of claim 1 conducted under essentially atmospheric pressure.

* * * * *

UNITED STATES PATENT AND TRADEMARK OFFICE
CERTIFICATE OF CORRECTION

PATENT NO. : 5,648,490
DATED : July 15, 1997
INVENTOR(S) : THALHAMMER et al.

It is certified that error appears in the above-identified patent and that said Letters Patent is hereby corrected as shown below:

In column 1, line 14, delete "to".

In column 1, line 14, delete "there is described" and insert therefor -- describes --.

In column 1, line 66, after "invention", insert -- as --.

In column 2, line 11, delete "therefor".

In column 2, line 26, delete "used".

In column 2, line 32, after "to" insert -- be --.

In column 2, line 33, delete "are".

In column 2, line 57, after "catalyst" insert -- , --.

In column 3, line 33, after "(0.2 mol)" insert -- of --.

In column 3, line 34, after "(DAHNP)", delete -- of --.

In Claim 1, column 5, line 28, before "carbon", insert -- 4 --.

In Claim 1, column 5, line 28, after "atoms", delete -- comprising --.

Signed and Sealed this

Twentieth Day of June, 2000

Attest:

Q. TODD DICKINSON

*Attesting Officer*        *Director of Patents and Trademarks*